United States Patent [19]

Carr

[11] 4,089,893

[45] May 16, 1978

[54] 2,2,2-TRIS(HYDROXYMETHYL)ETHYL-PHOSPONIC ACID AND METHOD FOR ITS PREPARATION

[75] Inventor: Lawrence J. Carr, Elk Grove Village, Ill.

[73] Assignee: Borg-Warner Corporation, Chicago, Ill.

[21] Appl. No.: 750,101

[22] Filed: Dec. 13, 1976

[51] Int. Cl.$^2$ ............................................... C07F 9/38
[52] U.S. Cl. ............................... 260/502.4 R; 210/58; 252/180
[58] Field of Search ............................... 260/502.4 R

[56] References Cited

U.S. PATENT DOCUMENTS

| | | | |
|---|---|---|---|
| 2,573,568 | 10/1951 | Harman et al. | 260/961 |
| 3,270,091 | 8/1966 | Spivack | 260/502.4 R |
| 3,271,306 | 9/1966 | Capriati et al. | 260/502.4 R |
| 3,483,279 | 12/1969 | Davis et al. | 260/969 |
| 3,493,639 | 2/1970 | Tavs | 260/502.4 R |
| 3,925,455 | 12/1975 | Maier | 260/502.4 P |
| 3,926,801 | 12/1975 | Quinlan | 210/58 |
| 3,933,427 | 1/1976 | Bohnsack et al. | 21/2.7 A |
| 3,963,636 | 6/1976 | Harris et al. | 252/181 |
| 3,966,630 | 6/1976 | Quinlan | 252/180 |
| 3,978,166 | 8/1976 | Hechenbleikier | 260/969 |

FOREIGN PATENT DOCUMENTS

| | | | |
|---|---|---|---|
| 1,369,429 | 10/1974 | United Kingdom. | |
| 245,098 | 10/1969 | U.S.S.R. | 260/502.4 R |

OTHER PUBLICATIONS

"A Report to Water Treatment Service Companies" (Monsanto).

Primary Examiner—Joseph E. Evans
Attorney, Agent, or Firm—Joseph Shekleton

[57] ABSTRACT

This invention relates to a novel phosphonic acid, 2,2,2-tris (hydroxymethyl) ethylphosphonic acid, and to a process for its preparation. It also relates to the use of such phosphonic acid as an inhibitor of corrosion of metal surfaces and as an inhibitor of the development of scale in cooling water.

1 Claim, No Drawings

2,2,2-TRIS(HYDROXYMETHYL)ETHYLPHOSPONIC ACID AND METHOD FOR ITS PREPARATION

It has been discovered in accordance with the present invention that the phosphonic acid of the structure

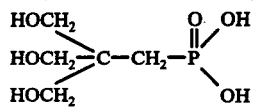

known as tris(hydroxymethyl)ethylphosphonic acid, or more precisely, as 3-hydroxy-2,2-bis(hydroxymethyl)-propylphosphonic acid, is obtained by hydrolysis of a polyphosphonic acid having

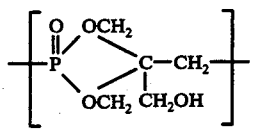

as its repeating unit. The hydrolysis reaction is accomplished quite simply, merely by heating with water, no catalyst or unusual conditions being required.

The polyphosphonic acid is available from the polymerization of pentaerythritol phosphite which is characterized by the structure

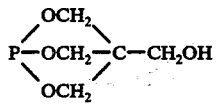

This polymerization is disclosed in U.S. Pat. No. 3,978,166; it is carried out by heating pentaerythritol phosphite at a relatively high temperature, i.e., from about 160° to about 250° C, until the polymerization is complete; usually, this requires at least about four hours, depending upon the particular temperature used.

The tris(hydroxymethyl)ethylphosphonic acid is an effective water treatment additive. That is, in the case of cooling water, it can be used to prevent the development of scale. Its efficacy in this respect is shown by data obtained from a scale inhibition test carried out as follows: Test solutions (A through F) of calcium chloride, sodium bicarbonate, sodium carbonate, tris(hydroxymethyl)ethylphosphonic acid and sodium hydroxide are prepared so as to give a solution containing 800 ppm of dissolved calcium carbonate, 12.5 (or 25.0) ppm of the phosphonate, and a pH of 9.0. The resulting mixture is maintained at room temperature for a period of time. At this point the calcium ion concentration, expressed as calcium carbonate, is determined and compared with the calcium ion concentration of the same solution, also kept at room temperature for the same period, but without the phosphonate present. The formation of scale involves the precipitation of calcium carbonate, so that a relatively high calcium ion concentration indicates effective scale inhibition.

The precent scale inhibition (PSI) is calculated according to the formula $$PSI = \frac{V_1 - V_0}{V_2 - V_0} \times 100$$

where
- $V_1$ = Calcium concentration with phosphonate inhibitor;
- $V_0$ = Calcium concentration without phosphonate inhibitor; and
- $V_2$ = Calcium concentration (800 ppm) at start of test.

The results are shown in Table I. Test solution E is as described above; test solutions B, C, D and F are the same except that the phosphonic acid content is neutralized by the addition of zinc dust; test solution A is similar to E except that it also contains 12.5 ppm of $ZnCl_2$. In each case, i.e., test solutions A through F, the test solution is compared with a solution which is similar except that it contains no phosphonate.

Table I

| Test Solutions | Phosphonate (ppm) | % Scale Inhibition | | | |
|---|---|---|---|---|---|
| | | 48 Hrs. | 72 Hrs. | 120 Hrs. | 168 Hrs. |
| A | 12.5 | 41 | | | 32 |
| B | 12.5 | 43 | | | 36 |
| C | 25.0 | | 28 | | |
| D | 12.5 | | | 55* | |
| E | 12.5 | 17 | | | 3 |
| F | 12.5 | 27 | | | 30 |

*70° C for 24 hours then room temperature for 96 hours.

Another test which is effective to demonstrate the scale inhibiting properties of the phosphonic acid herein depends on the amount of scale which adheres to the wall surface of a container. The percent scale inhibition in such instances is calculated according to the formula $$PSI = \frac{Wc - Wi}{Wc} \times 100$$

where
- $Wc$ = weight of scale adhering to the wall surface when phosphonate is present, and
- $Wi$ = weight of scale adhering to the wall surface when no phosphonate is present.

Test solutions similar to B, D and F (in Table I) are permitted to stand in a glass beaker and a copper beaker for 240 hours and 196 hours, respectively. The percent scale inhibition in each case is shown in Table II.

Table II

| Test Solutions | Wall Surface | 196 Hrs. | 240 Hrs. |
|---|---|---|---|
| G | glass | | 77 |
| H | copper | 65 | |

Effective scale-inhibiting concentrations of the phosphonic acid herein in water range from about 5 ppm to about 25 ppm.

The tris(hydroxymethyl)ethylphosphonic acid herein is effective also as an aqueous corrosion inhibitor. This is shown by the data in Table III. The data reflects results obtained from tests carried out in a synthetic hard water at room temperature. The "hard water" contains the following ingredients:
- 1.267 g. $Na_2CO_3$
- 4.987 g. $NaHCO_3$
- 8.039 g. $CaCl_2$
- 4.334 g. $MgSO_4$ per 18 liters of water. Its pH is 8.2. A 1008 mild steel coupon (1 × 1 × 3/16 inch) is suspended in the water for three days and the loss in weight noted. The water is agitated at room temperature all the while. The degree of corrosion is noted in terms of mils per year (mpy).

Table III

| | Phosphonic Acid ppm | Zn (as ZnCl$_2$) ppm | pH | mpy |
|---|---|---|---|---|
| 1. | 0 | 0 | 8.2 | 17.8 |
| 2. | 25 | 0 | 7.7 | 6.4 |
| 3. | 25 | 0 | 7.7 | 12.6 |
| 4. | 0 | 25 | 6.9 | 9.2 |
| 5. | 0 | 25 | 6.9 | 6.5 |
| 6. | 12.5 | 12.5 | 7.5 | 0.9 |
| 7. | 12.5 | 12.5 | 7.5 | 0.2 |
| 8. | 12.5 | 12.5 | 7.5 | 0.5 |
| 9. | 12.5 | 12.5 | 8.0 | 2.8 |
| 10. | 12.5 | 12.5 | 8.5 | 3.8 |

Effective corrosion-resisting concentrations of the phosphonic acid herein in water range from about 5 to about 1000 ppm.

It will be noted that, while both the phosphonic acid and zinc ion are effective inhibitors of corrosion, they also exhibit synergistic behavior when used together for this purpose. Thus, singly, they score from 6.4 to 12.6 whereas in combination the rating is from 0.5 to 3.8. The zinc is effective in concentrations ranging from about 5 ppm to about 1000 ppm.

The tris(hydroxymethyl)ethylphosphonic acid is effective also as a cement retarder, i.e., when added in small proportions to liquid cement it lengthens the time during which the cement hardens or sets.

The polymerization of pentaerythritol phosphite and hydrolysis of the resulting polyphosphonate is shown in the following examples.

EXAMPLE 1

A stoppered test tube (15 × 120 mm.) containing 7.0 g. (0.0427 mol) of pentaerythritol phosphite under dry nitrogen is heated at 180°–200° C for 7 hours. During this period the granular solid is converted to a fluid melt, then to a viscous liquid and finally to a glassy solid. The solid product is the desired polyphosphonate; it does not melt up to its decomposition temperature, which is about 285° C, nor is it soluble in any of several ordinary organic solvents.

EXAMPLE 2

The glassy solid product of Example 1 is mixed with 18 g. of water and heated with stirring at reflux temperature for 2 hours. The resulting solution is cooled and filtered yielding 0.15 g. of solid pentaerythritol. The filtrate is shown by iodometric titration to contain 20% of oxidizable phosphorus (phosphorous acid). NMR ($^{31}$P) analysis indicates three types of phosphorus: 20% as phosphorous acid; 60% as phosphonic acid; and 20% which is believed to be present as a cyclic phosphonate.

Water is removed from the filtrate by evaporation at diminished pressure yielding as the residue 8.7 g. of a very viscous amber syrup. Potentiometric titration shows two deflection points characteristic of a dibasic acid. The syrup is soluble in water and highly polar organic solvents. It readily forms an insoluble lead salt in neutral solution. NMR ($_1$H) analysis of an aqueous solution indicates the structure of the product to be 3-hydroxy-2,2-bis(hydroxymethyl)propylphosphonic acid.

All parts and percentages herein unless otherwise expressly stated are by weight.

I claim:

1.

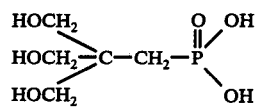

* * * * *